(12) United States Patent
Mashiach

(10) Patent No.: US 10,238,875 B2
(45) Date of Patent: Mar. 26, 2019

(54) SYSTEMS AND METHODS FOR HYPERTENSION CONTROL

(71) Applicant: Adi Mashiach, Tel Aviv (IL)

(72) Inventor: Adi Mashiach, Tel Aviv (IL)

( * ) Notice: Subject to any disclaimer, the term of this patent is extended or adjusted under 35 U.S.C. 154(b) by 0 days.

(21) Appl. No.: 14/653,891

(22) PCT Filed: Dec. 19, 2013

(86) PCT No.: PCT/IB2013/003215
§ 371 (c)(1),
(2) Date: Jun. 19, 2015

(87) PCT Pub. No.: WO2014/096969
PCT Pub. Date: Jun. 26, 2014

(65) Prior Publication Data
US 2015/0343221 A1    Dec. 3, 2015

Related U.S. Application Data

(60) Provisional application No. 61/739,701, filed on Dec. 19, 2012.

(51) Int. Cl.
*A61N 1/36* (2006.01)
*A61B 18/14* (2006.01)
(Continued)

(52) U.S. Cl.
CPC ...... *A61N 1/36117* (2013.01); *A61B 18/1492* (2013.01); *A61N 1/0551* (2013.01); *A61N 1/36057* (2013.01); *A61N 1/36125* (2013.01); *A61N 1/37223* (2013.01); *A61B 2018/00404* (2013.01); *A61B 2018/00434* (2013.01); *A61B 2018/00577* (2013.01); *A61B 2018/1465* (2013.01)

(58) Field of Classification Search
None
See application file for complete search history.

(56) References Cited

U.S. PATENT DOCUMENTS 6,738,655 B1 * 5/2004 Sen ..................... A61B 5/0422
                                                    600/374
9,248,291 B2 * 2/2016 Mashiach ............ A61N 1/0551
(Continued)

OTHER PUBLICATIONS

International Search Report dated Nov. 25, 2014, issued in corresponding international application No. PCT/IB13/03215 (5 pages).
(Continued)

*Primary Examiner* — Ankit D Tejani
(74) *Attorney, Agent, or Firm* — Finnegan, Henderson, Farabow, Garrett & Dunner, LLP

(57) ABSTRACT

Systems and methods for hypertension control via energy delivery to one or more nerves affecting blood pressure are provided. Systems may include implantable devices configured for non-contacting neuromodulation. Implantable devices may be configured for intravascular implantation. Systems may also include external devices configured to communicated with implantable neuromodulation devices, Additional systems may include non-implantable devices for delivering modulation energy and ablation energy to one or more nerves affecting blood pressure.

27 Claims, 10 Drawing Sheets

(51) Int. Cl.
*A61N 1/05* (2006.01)
*A61N 1/372* (2006.01)
*A61B 18/00* (2006.01)

(56) References Cited

U.S. PATENT DOCUMENTS

| | | | | |
|---|---|---|---|---|
| 2007/0265687 | A1* | 11/2007 | Deem | A61B 18/1492 607/72 |
| 2009/0024195 | A1 | 1/2009 | Rezai et al. | |
| 2010/0305638 | A1* | 12/2010 | McCabe | A61N 1/3706 607/11 |
| 2011/0264075 | A1* | 10/2011 | Leung | A61B 18/082 604/528 |
| 2011/0307034 | A1* | 12/2011 | Hastings | A61B 18/1206 607/61 |
| 2012/0035711 | A1 | 2/2012 | Gross et al. | |

OTHER PUBLICATIONS

Written Opinion of the International Searching Authority dated Nov. 25, 2014, issued in corresponding international application No. PCT/IB13/03215 (7 pages).

* cited by examiner

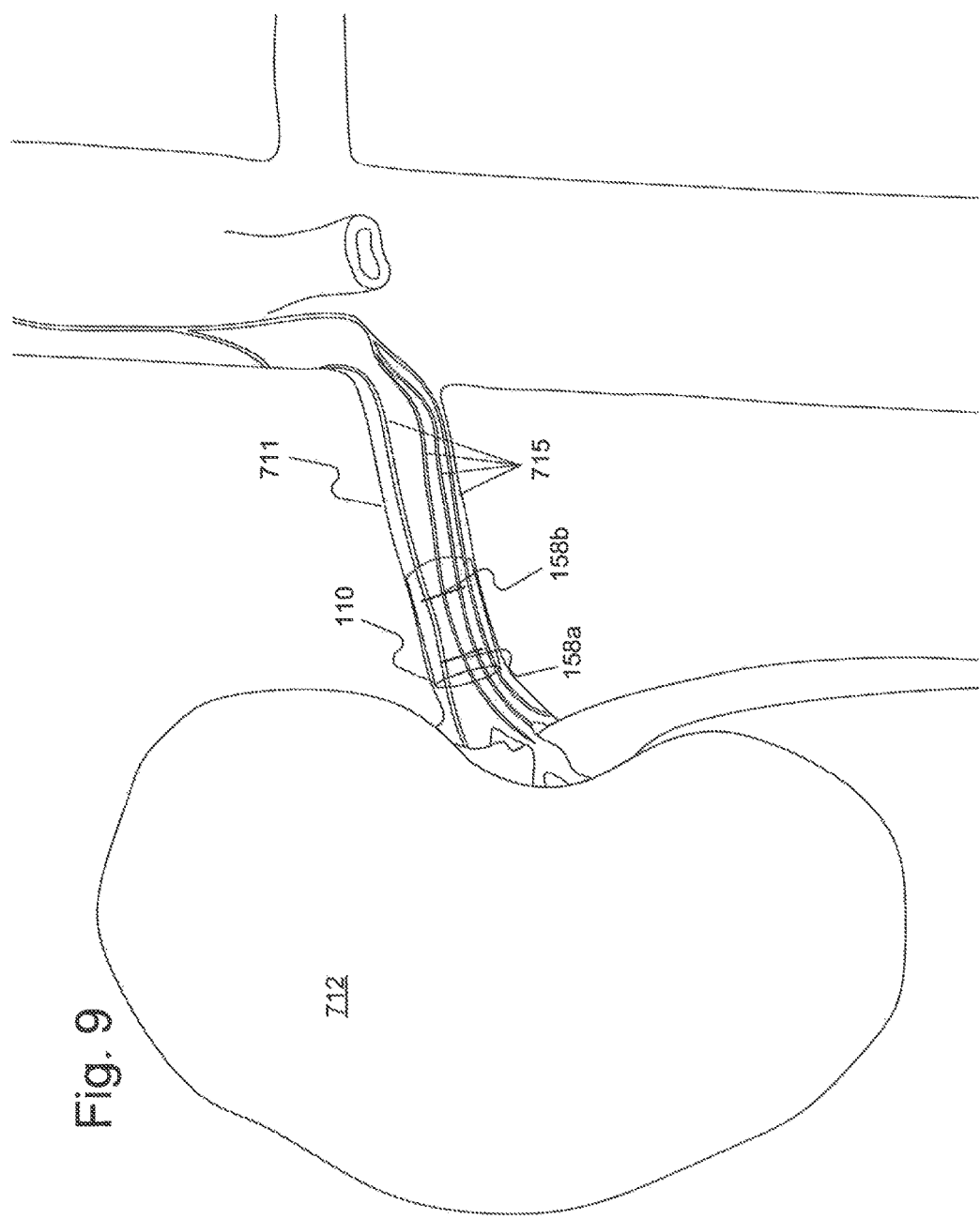

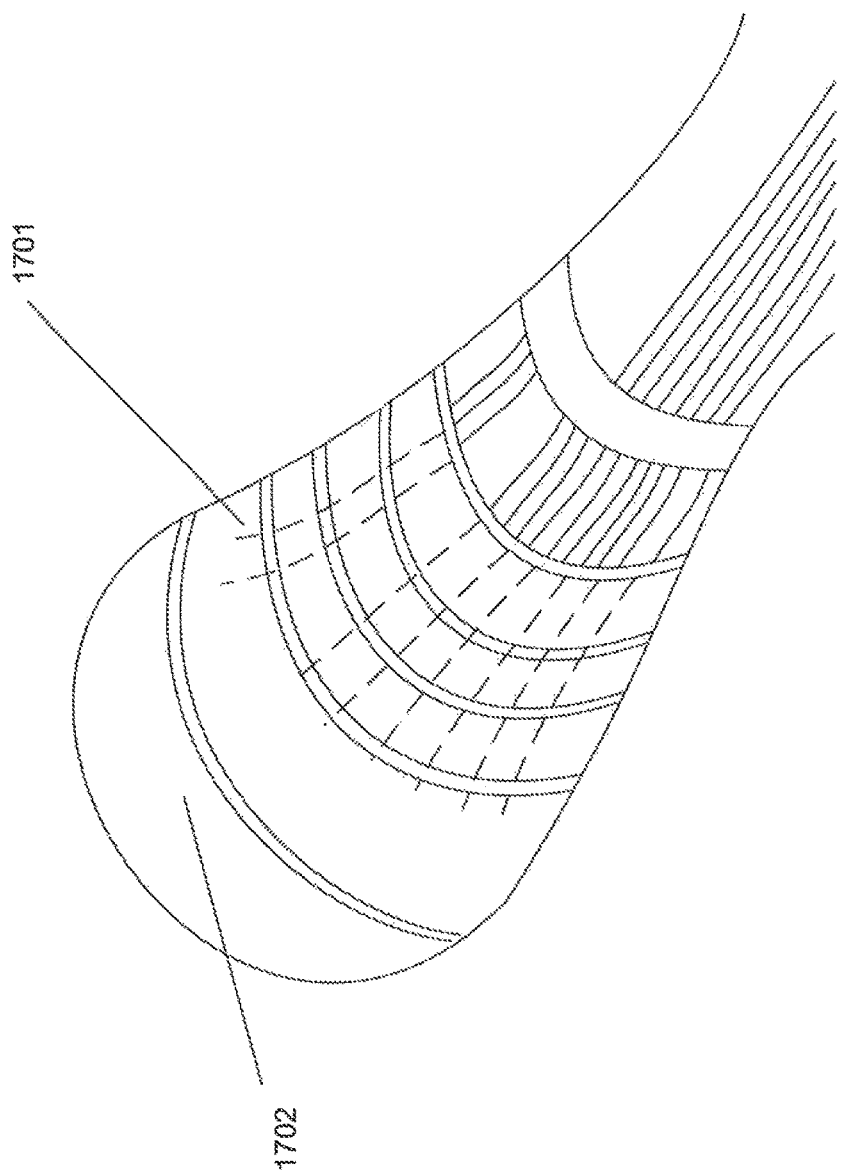

SYSTEMS AND METHODS FOR HYPERTENSION CONTROL

RELATED APPLICATIONS

This application is a National Stage Entry of PCT/IB2013/003215, filed on Dec. 19, 2013, and claims the benefit of priority under 35 U.S.C. § 119(e) of U.S. Provisional Patent Application No. 61/739,701, filed on Dec. 19, 2012, the disclosures of each of which is hereby incorporated by reference.

TECHNICAL FIELD

Embodiments of the present disclosure generally relate to devices and methods for modulating or otherwise affecting a nerve. More particularly, embodiments of the present disclosure relate to devices and methods for modulating or affecting a nerve through the delivery of energy via an implantable or non implantable electrical modulator.

BACKGROUND

Neural modulation presents the opportunity to treat many physiological conditions and disorders by interacting with the body's own natural neural processes. Neural modulation includes inhibition (e.g., blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g., through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

Other conditions for which neuromodulation may be an effective treatment include sleep disordered breathing and head pain. The foregoing are just a few examples of conditions to which neuromodulation may be of benefit, however embodiments of the invention described hereafter are not necessarily limited to treating only the above-described conditions.

SUMMARY

An exemplary embodiment disclosed herein includes a hypertension therapy device. The hypertension therapy device may include a carrier configured for deployment in vasculature of a subject, an antenna located on the carrier, at least one electrode arranged for deployment with the carrier, the at least one electrode being arranged so as to create an electric field when the electrode is energized, at least a portion of a circuit arranged for intravascular deployment with the carrier within a blood vessel, the circuit portion being electrically connected to the at least one electrode, the circuit portion further being configured to deliver an electrical signal to the at least one electrode. In the hypertension therapy device, the at least one electrode may be configured to emit from within an interior of the blood vessel an electrical field sufficient to modulate signals of at least one nerve located outside of the interior of the blood vessel the vasculature.

In another exemplary embodiment, an intravascular device for hypertension therapy may include a carrier configured for deployment in a blood vessel via an intravascular deployment mechanism, a plurality of electrode contacts arranged circumferentially about the carrier. The electrode contacts may be configured to receive energy from a source and to radiate energy via the plurality of electrical contacts to a plurality of locations on a wall of the blood vessel.

In yet another exemplary embodiment, a method for treating a medical condition affected by a nerve may include, no more than three times a day, orienting a power source external to a body of a patient and adjacent to a location within the body where a transceiver is implanted, the transceiver being implanted at a location proximate the nerve and being configured to receive an alternating current signal from a power source outside the patient's body and being tuned to convert the received signal into an alternating current electrical field encompassing the nerve. The method may further include no more than three times a day, wirelessly transmitting power from the power source to the implanted transceiver, for less than 10 seconds to deliver energy in an amount greater than 2 watts and to thereby cause to cause temporary nerve paralysis.

In yet another exemplary embodiment, a device for paralyzing a nerve may include a carrier configured for implantation within a body of a patient, an antenna associated with the carrier, the antenna being configured to receive a wireless power signal from a source outside the patient's body, a circuit portion associated with the implant carrier and connected to the antenna, at least one electrode on the implant carrier, the at least one electrode being configured to cooperate with the circuit portion and the antenna, and being sized and shaped to generate an electrical field sufficient to paralyze a nerve when the implant is in a vicinity of a nerve inside the patient's body and in response to energy received from the external source.

In yet another exemplary embodiment, a device may include a housing configured for location external to a body of a subject, at least one processor associated with the housing and configured for electrical communication with a power source, and an antenna associated with the at least one processor. The at least one processor may be configured to communicate with a circuit implanted in a subject's vasculature, and adjust delivery of power from the power source to the implanted circuit based on a dynamic biological condition of the subject.

In yet another exemplary embodiment, a method for treating hypertension may include delivering an implantable device to an intravascular location in a vicinity of a subject's carotid baroreceptors, the implantable device comprising at least one electrode, and stimulating the subject's baroreflex via the at least one of electrode in order to control hypertension.

In yet another exemplary embodiment, a method for treating hypertension may include affixing an antenna to a subject's skin, the antenna being connected to at least one processor and a power source, transmitting, via the antenna, a signal to an implantable device deployed in the subject's vascular system in a location in a vicinity of a carotid baroreceptor, the signal being configured to cause modulation of the subject's baroreflex by at least one pair of electrodes located on the implantable device.

In yet another exemplary embodiment, a device may comprise an intravascular delivery mechanism configured to deliver an intravascular implant to a location in at least one of a carotid artery and a jugular vein of a subject via at least one of an axillary artery and a jugular vein of the subject, the intravascular implant being removably secured to a distal end of the intravascular delivery mechanism. The intravascular delivery mechanism may include a carrier configured for intravascular delivery, at least one electrode arranged for delivery with the carrier, the at least one electrode being configured and tuned to stimulate a glossopharyngeal nerve upon reception of a power signal sent from a location external to the subject's body, and a circuit portion arranged for intravascular delivery with the carrier, the circuit portion being electrically connected to the at least one electrode.

In yet another exemplary embodiment, a device may include an intravascular delivery mechanism configured to deliver an intravascular implant to a location in a cerebral blood vessel in the brain of a subject, the intravascular implant being secured to a distal end of the intravascular delivery mechanism. The intravascular implant may include a carrier configured for intravascular cerebral delivery, at least one electrode sized and arranged for delivery to subject's brain. The electrode may be configured to perform at least one of the following functions deliver energy to brain tissue and detect feedback from brain tissue.

In yet another exemplary embodiment, a method of orienting an intravascular device may include delivering the intravascular device to an implant location in vasculature of a subject's body, the intravascular device including a carrier and an antenna, arranging an external antenna outside the body of the subject, the external antenna being electrically connected to a power source, transmitting a wireless signal from the external antenna to the antenna of the intravascular device, detecting a level of coupling between the external antenna and the antenna of the intravascular device, adjusting a relative position of the intravascular device until a level of coupling exceeds a predetermined threshold, and fixing the position of the intravascular device within the vasculature of the subject when the predetermined threshold is exceeded.

In yet another exemplary embodiment, a device for orienting an implant delivered on a catheter, the implant including a micro-antenna, may include at least one processor. The at least one processor may be configured to control delivery of a wireless power signal via an antenna located external to a body of a subject, process coupling feedback from the micro-antenna resulting from the delivered wireless power signal, compare the coupling feedback with a threshold, and signal when the threshold is met.

In yet another exemplary embodiment, a device may include a carrier configured for deployment in vasculature of a subject, an antenna arranged for intravascular deployment with the carrier, and a radiopaque marker arranged for intravascular deployment with the carrier, wherein the radiopaque marker and the antenna are arranged in fixed circumferential positions with respect to one another.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIG. 9 depicts an exemplary implant location for the treatment of hypertension.

FIG. 10 depicts an exemplary embodiment of a device configured for renal artery ablation.

DESCRIPTION OF EXEMPLARY EMBODIMENTS

Figure 1:
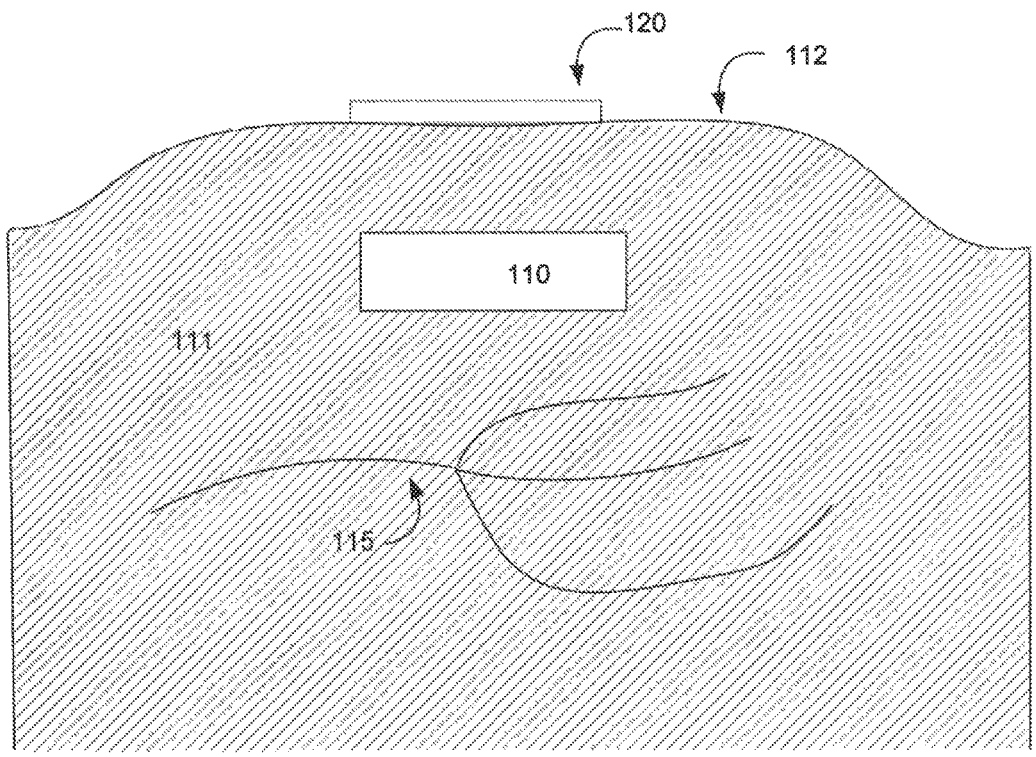
FIG. 1 schematically illustrates an implant unit and external unit, according to an exemplary embodiment of the present disclosure.

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for modulating or otherwise affecting a nerve through the delivery of energy. Nerve modulation, or neural modulation, includes inhibition (e.g., blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may including providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied. Nerves may also be affected in other ways through energy delivery, for example, by ablation, which serves to permanently damage or eliminated the ability of a neuron to conduct nervous signals.

In the treatment of hypertension, for example, neural modulation may be used to increase, decrease, eliminate or otherwise modify nerve signals generated by the body to regulate blood pressure. In patients with sleep disordered breathing, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain.

While some embodiments of the present disclosure may be disclosed for use in patients with specific conditions, the embodiments may be used in conjunction with any patient/portion of a body where nerve modulation may be desired. That is, in addition to use in patients with hypertension, sleep disordered breathing, or migraine headaches, embodiments of the present disclosure may be use in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

In some embodiments consistent with the present disclosure, an implant unit is utilized to deliver neuromodulation. In alternative embodiments, a neuromodulating device is delivered to a vicinity of a nerve to be modulated through alternative means, including, for example, a catheter. Throughout the disclosure, discussion of apparatuses and methods for generating electric fields sufficient to modulate a target nerve may be applicable to both implantable and non-implantable devices.

FIG. 1 illustrates an implant unit and external unit, according to an exemplary embodiment of the present disclosure. An implant unit 110, may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, arterial walls, venous walls, and any other type of biological tissue. Thus, location of implant unit 110 does not require contact with nerve 115 for effective neuromodulation. A more detailed discussion of non contacting neuromodulation is provided below with respect to FIGS. 6a, 6b, 6c. The implant unit 110 may also be located directly adjacent to nerve 115, such that no intervening tissue 111 exists.

Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve. Further details regarding implantation locations of an implant unit 110 for treatment of hypertension are provided below, with respect to FIGS. 8 and 9.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Further embodiments, described below with respect to FIG. 10, describe apparatuses and methods by which hypertension may be treated via techniques that do not incorporate an implantable device, but rely on other delivery methods, for example, a catheter, to bring ablation electrodes into the vicinity of a nerve to be ablated.

Figure 2:
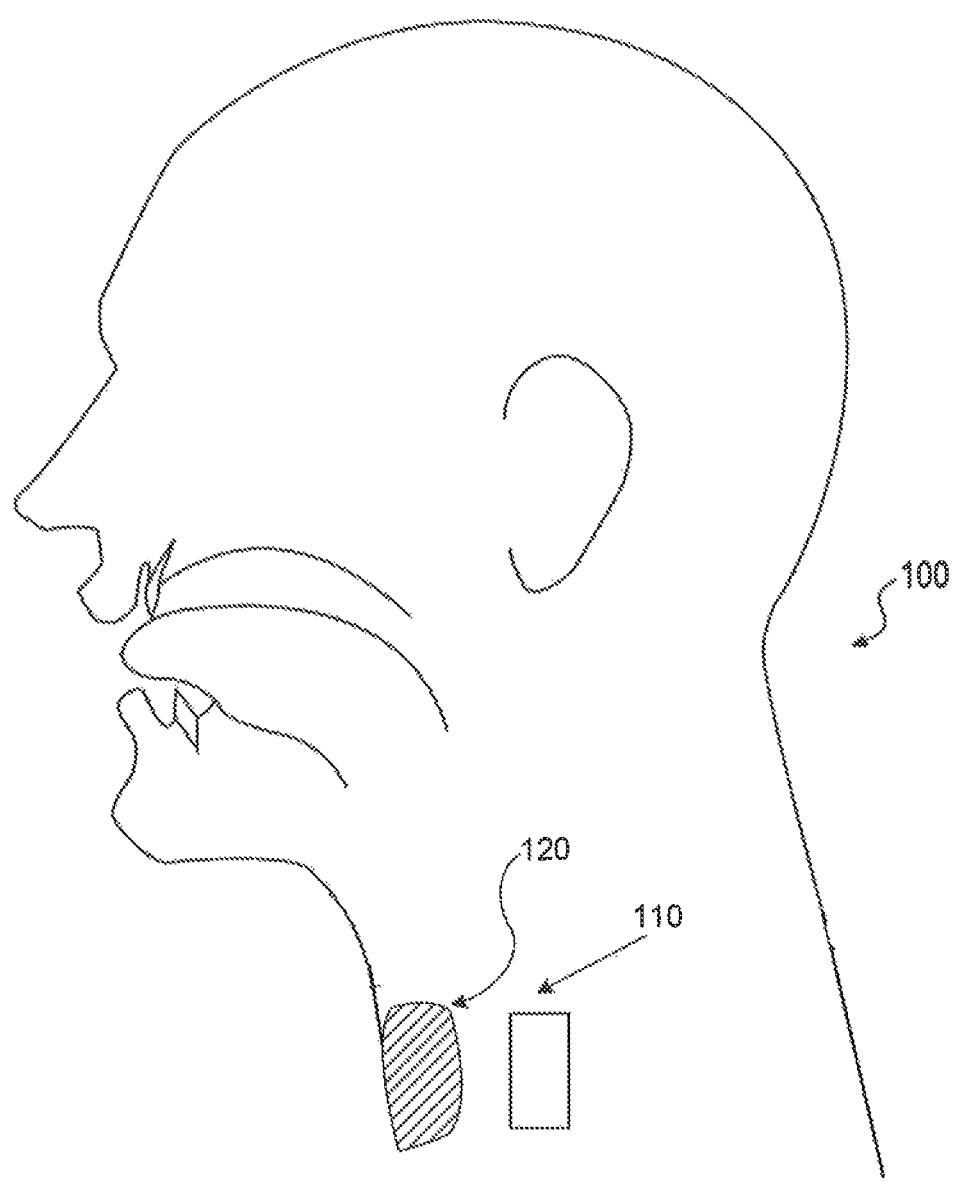
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with hypertension. The system may include an external unit 120 that may be configured for location external to the patient. As illustrated in FIG. 2, external unit 120 may be configured to be affixed to the patient 100. FIG. 2 illustrates that in a patient 100 with hypertension, the external unit 120 may be configured for placement on the patient's neck to communicate with an implant unit 110 located in the patient's carotid artery. The suitability of placement locations may be determined by communication between external unit 120 and implant unit 110, discussed in greater detail below. Alternate embodiments, wherein implant unit 110 is located near a different nerve to be modulated and external unit 120 is located on the skin to communicate with implant unit 110 are discussed in greater detail below.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing. The housing may include any suitable container configured for retaining components. In addition, while the external unit is illustrated schematically in FIG. 2, the housing may be any suitable size and/or shape and may be rigid or flexible. Non-limiting examples of housings for the external unit 100 include one or more of patches, buttons, or other receptacles having varying shapes and dimensions and constructed of any suitable material. In one embodiment, for example, the housing may include a flexible material such that the external unit may be configured to conform to a desired location. For example, as illustrated in FIG. 2, the external unit may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the housing may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
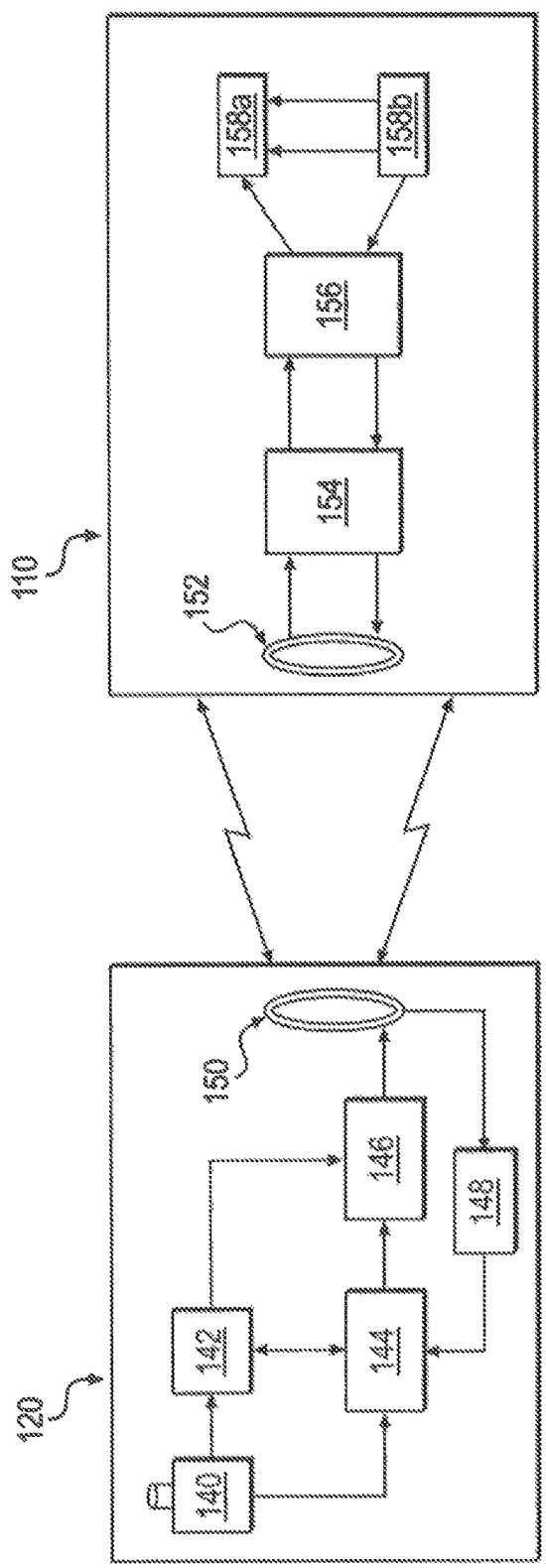
FIG. 3 schematically illustrates a system including an implant unit and an external unit, according to an exemplary embodiment of the present disclosure.

FIG. 3 schematically illustrates a system including external unit 120 and an implant unit 110. In some embodiments, internal unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removably couplable to the external unit at an exterior location relative to external unit. Alternatively, as shown in FIG. 3, power source 140 may be permanently or removably coupled to a location within external unit 120. The power source may further include any suitable source of power configured to be in electrical communication with the processor. In one embodiment, for example the power source 140 may include a battery.

The power source may be configured to power various components within the external unit. As illustrated in FIG. 3, power source 140 may be configured to provide power to the processor 144. In addition, the power source 140 may be configured to provide power to a signal source 142. The signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated one or more aspects of a signal. The amplifier may further be configured to output the amplified signals to one or more components within external unit 120.

The external unit may additionally include a primary antenna 150. The primary antenna may be configured as part of a circuit within external unit 120 and may be coupled either directly or indirectly to various components in external unit 120. For example, as shown in FIG. 3, primary antenna 150 may be configured for communication with the amplifier 146.

The primary antenna may include any conductive structure that may be configured to create an electromagnetic field. The primary antenna may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. The primary antenna may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil antenna. Such a coil antenna may be made from any suitable conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. The size of a coil antenna suitable for use as a primary antenna may be based on the location of implant unit 110. For example, when implant unit 110 is located closer to the surface of the skin, a smaller primary antenna may provide successful communication. A coil antenna suitable for use as primary antenna 150 may have any number of windings, e.g. 4, 8, 12, or more. A coil antenna suitable for use as primary antenna 150 may have a wire diameter between about 0.1 mm and 2 mm. These antenna parameters are exemplary only, and may be adjusted above or below the ranges given to achieve suitable results.

As noted, implant unit 110 may be configured to be implanted in a patient's body (e.g., beneath the patient's skin). FIG. 2 illustrates that the implant unit 110 may be configured to be implanted for modulation of a nerve located in a subject's neck region. Such a nerve may include, for example, an afferent neuron transmitting a blood pressure signal. Such an afferent nerve may include the glossopharyngeal nerve, which is the pathway for blood pressure signals communicated from the carotid baroreceptors.

Modulation of parasympathetic nerve fibers on and around the renal arteries (i.e., the renal nerves) and/or the vagus nerve may also be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible tubular carrier 161 (FIGS. 4a and 4b) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a size and configuration suitable for conforming to the anatomy in which it is implanted. For example, when implanting in a patient's vasculature, flexible carrier 161 may be configured as a tube. Configured as a tube, flexible carrier 161 may be configured to expand when implanted so as affix itself to the walls of the blood vessel in which it is implanted.

Other components that may be included in or otherwise associated with the implant unit are illustrated in FIG. 3. For example, implant unit 110 may include a secondary antenna 152 mounted onto or integrated with flexible carrier 161. Similar to the primary antenna, the secondary antenna may include any suitable antenna known to those skilled in the art that may be configured to send and/or receive signals. The secondary antenna may include any suitable size, shape, and/or configuration. The size, shape and/or configuration may be determined by the size of the patient, the placement location of the implant unit, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a rectangular shape (see also FIG. 4b) or circular shape or oval shape. Such a coil antenna may be made from any suitable conductive material and may be configured to include any suitable arrangement of conductive coils (e.g., diameter, number of coils, layout of coils, etc.). A coil antenna suitable for use as secondary antenna 152 may have a diameter of between about 1 mm and 30 mm, and may be rectangular, circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.01 mm and 1 mm. These antenna parameters are exemplary only, and may be adjusted above or below the ranges given to achieve suitable results.

Figure 4:
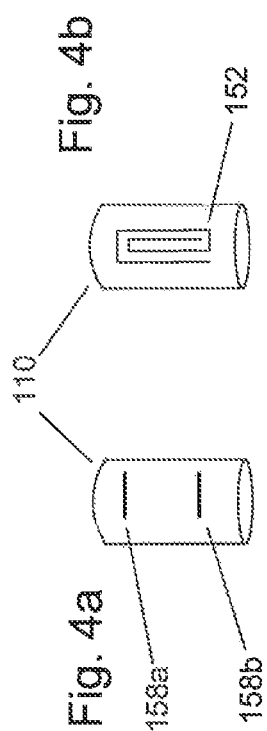
FIGS. 4a and 4b depicts an exemplary implant unit for intravascular implantation.

Implant unit 110 may additionally include a plurality of field-generating implant electrodes 158a, 158b. The electrodes may include any suitable shape and/or orientation on the implant unit so long as the electrodes may be configured to generate an electric field in the body of a patient. Implant electrodes 158a and 158b may be configured for implantation into the body of a subject in the vicinity of one or more nerves either together with or separate from implant unit 110. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, point electrodes, circular electrodes, conductive loops, and/or circular pairs of electrodes. In some embodiments, implant unit 110 may be configured in a tubular shape. In such embodiments, conductive loop electrodes may be positioned to wrap around the tubular implant unit 110. As shown in FIG. 4a, electrodes 158a and 158b may be located directly on flexible carrier 161. The electrodes may be located on any portion of implant unit 110. Additionally, implant unit 110 may include electrodes located at a plurality of locations, for example on either end of flexible carrier 161. Electrodes on different sides of the implant unit may be activated sequentially or simultaneously to generate respective electric fields. Implant electrode pairs may be spaced apart from one another by a distance of less than about 25 mm. Implant electrodes may have a thickness between about 200 nanometers and 1 millimeter, and may have a surface area of about 0.01 $mm^2$ to about 80 $mm^2$. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm and 7 mm. In other embodiments, anode and cathode electrode pairs may be spaced apart by a distance of approximately 6 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

As noted, electrodes 158a and 158b may configured to be implanted into the body of a subject in the vicinity of at least one nerve to be modulated. Implant (or modulation) electrodes 158a and 158b may be configured to receive an applied electric signal in response to the signal received by the antenna and generate an electrical field to modulate the at least one nerve from a position where the at least one pair of modulation electrodes does not contact the at least one nerve.

FIGS. 4a and 4b provides a schematic representation of an exemplary configuration of implant unit 110. As illustrated in FIGS. 4a and 4b, in one embodiment, the field-generating electrodes 158a and 158b may include two electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, an expandable structure, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. Implant unit 110 may be constructed in various shapes. In some embodiments, implant unit may appear substantially as illustrated in FIGS. 4a and 4b. In other embodiments, implant unit 110 may have additional or different structures in different orientations. In some embodiments, the shape of implant unit 110 (e.g., as shown in FIGS. 4a and 4b) may facilitate orientation of implant unit 110 with respect to a particular nerve to be modulated. Thus, other regular or irregular shapes may be adopted in order to facilitate implantation in differing parts of the body.

As illustrated in FIGS. 4a and 4b, secondary antenna 152 and electrodes 158a, 158b may be mounted on or integrated with flexible carrier 161. Various circuit components and connecting wires (discussed further below) may be used to connect secondary antenna with implant electrodes 158a and 158b. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include silicone, polyimides, phenyltrimethoxysilane (PTMS), polymethyl methacrylate (PMMA), Parylene C, liquid polyimide, laminated polyimide, polyimide, Kapton, black epoxy, polyether ketone (PEEK), Liquid Crystal Polymer (LCP), or any other suitable biocompatible coating. In some embodiments, the protective coating may include a plurality of layers, including different materials or combinations of materials in different layers.

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158a, 158b, etc, Amplifier 146 may output the amplified signal to primary antenna 150.

External unit 120 may communicate a primary signal on primary antenna to the secondary antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. In some embodiments, coupling between the primary and secondary antennas may include capacitive coupling, inductive coupling, radiofrequency coupling, etc. and any combinations thereof.

Coupling between primary antenna 150 and secondary antenna 152 may depend on the proximity of the primary antenna relative to the secondary antenna, That is, in some embodiments, an efficiency or degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b.

Figure 5:
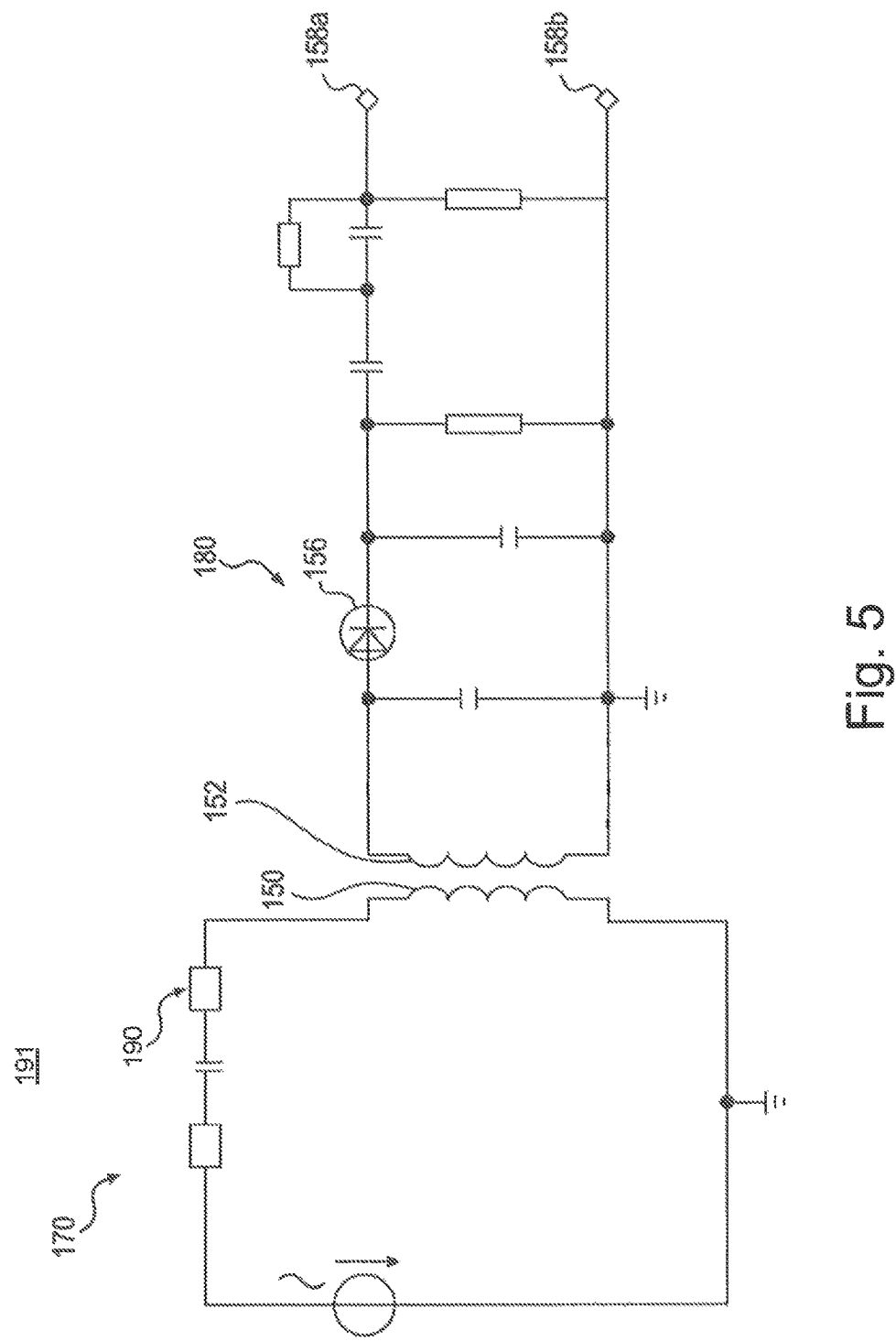
FIG. 5 illustrates circuitry of an implant unit and an external unit, according to an exemplary embodiment of the present disclosure.

FIG. 5 illustrates circuitry 170 that may be included in external unit 120 and circuitry 180 that may be included in implant unit 110. Additional, different, or fewer circuit components may be included in either or both of circuitry 170 and circuitry 180. As shown in FIG. 5, secondary antenna 152 may be arranged in electrical communication with implant electrodes 158a, 158b. In some embodiments, circuitry connecting secondary antenna 152 with implant electrodes 158a and 158b may cause a voltage potential across implant electrodes 158a and 158b in the presence of a secondary signal on secondary antenna 152. For example, an implant unit 110 may apply a voltage potential to implant electrodes 158a and 158b in response to an AC signal received by secondary antenna 152. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

The field inducing signal may be generated as a result of conditioning of the secondary signal by circuitry 180. As shown in FIG. 5, circuitry 170 of external unit 120 may be configured to generate an AC primary signal on primary antenna 150 that may cause an AC secondary signal on secondary antenna 152. In some exemplary embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b. In some embodiments, all or substantially all of the power delivered to electrodes 158a and 158 may be received from a source external to the body.

As noted above, the field inducing signal may be configured to generate an electric field between implant electrodes 158a and 158b. In some instances, the magnitude, energy density, and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be modulated; whether the nerve is branched; orientation of the induced electric field with respect to the nerve; type of tissue present between the electrodes and the nerve; etc.). For example, the modulation signal may include a voltage between about 0.5 volts and about 40 volts or electric current between about 50 microamps and about 20 milliamps.

In some embodiments, the electrodes 158a and 158b may generate an electric field configured to penetrate intervening tissue 111 between the electrodes and one or more nerves. The intervening tissue 111 may include muscle tissue, bone, connective tissue, adipose tissue, organ tissue, or any combination thereof. In some embodiments, the electrodes 158a and 158b may be configured such that they, when implanted in a location within an interior blood vessel, generate an electric field configured to modulate a nerve located outside the interior of the blood vessel.

Figure 6A:
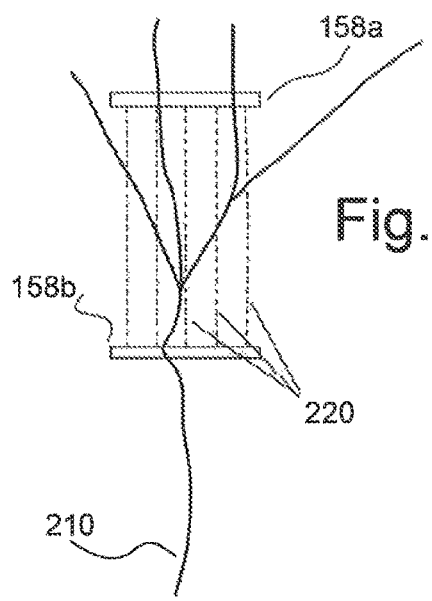
FIG. 6a illustrates a pair of electrodes spaced apart from one another along the longitudinal direction of a nerve to facilitate generation of an electric field having field lines substantially parallel to the longitudinal direction of nerve.
Figure 6B:
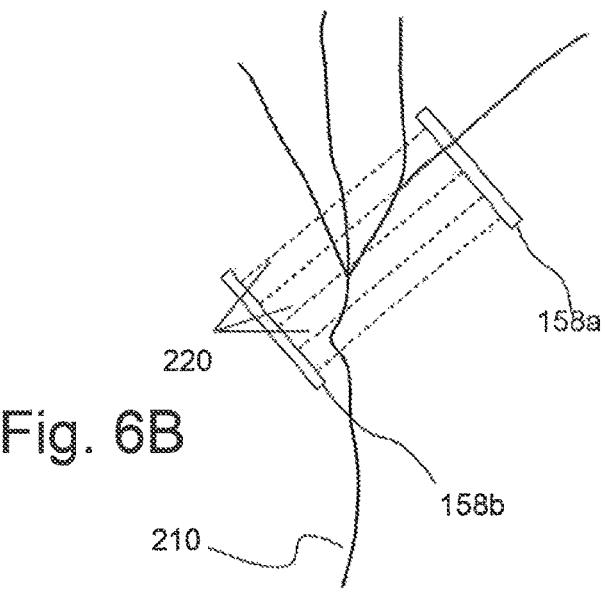
FIG. 6b illustrates an embodiment wherein electrodes are spaced apart from one another in a longitudinal direction of at least a portion of nerve.
Figure 6C:
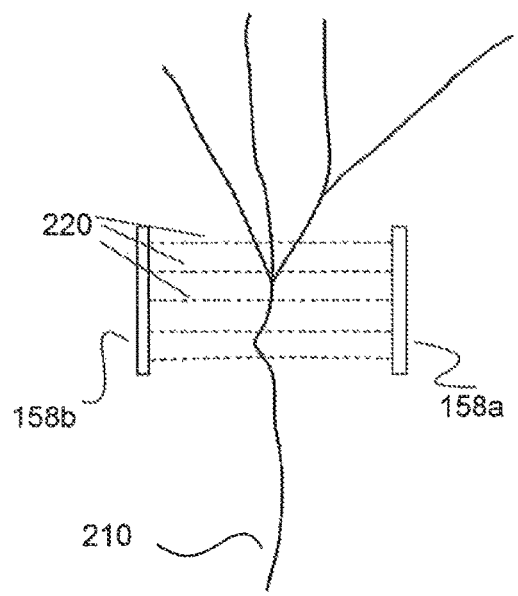
FIG. 6c illustrates a situation wherein electrodes are spaced apart from one another in a transverse direction of nerve.

The generation of electric fields configured to penetrate intervening tissue is now discussed with respect to FIGS. 6a, 6b, 6c. In response to a field inducing signal, implant electrodes 158a and 158b may be configured to generate an electric field with field lines extending generally in the longitudinal direction of one or more nerves to be modulated. In some embodiments, implant electrodes 158a and 158b may be spaced apart from one another along the longitudinal direction of a nerve to facilitate generation of such an electric field. The electric field may also be configured to extend in a direction substantially parallel to a longitudinal direction of at least some portion of the nerve to be modulated. For example, a substantially parallel field may include field lines that extend more in a longitudinal direction than a transverse direction compared to the nerve. Orienting the electric field in this way may facilitate electrical current flow through a nerve or tissue, thereby increasing the likelihood of eliciting an action potential to induce modulation.

FIG. 6a illustrates a pair of electrodes 158a, 158b spaced apart from one another along the longitudinal direction of nerve 210 to facilitate generation of an electric field having field lines 220 substantially parallel to the longitudinal direction of nerve 210. In FIG. 6a, modulation electrodes 158a, 158b are illustrated as line electrodes, although the generation of substantially parallel electric fields may be accomplished through the use of other types of electrodes, for example, a series of point electrodes. Utilizing an electric field having field lines 220 extending in a longitudinal direction of nerve 210 may serve to reduce the amount of energy required to achieve neural modulation.

Naturally functioning neurons function by transmitting action potentials along their length. Structurally, neurons include multiple ion channels along their length that serve to maintain a voltage potential gradient across a plasma membrane between the interior and exterior of the neuron. Ion channels operate by maintaining an appropriate balance between positively charged sodium ions on one side of the plasma membrane and negatively charged potassium ions on the other side of the plasma membrane. A sufficiently high voltage potential difference created near an ion channel may exceed a membrane threshold potential of the ion channel. The ion channel may then be induced to activate, pumping the sodium and potassium ions across the plasma membrane to switch places in the vicinity of the activated ion channel. This, in turn, further alters the potential difference in the vicinity of the ion channel, which may serve to activate a neighboring ion channel. The cascading activation of adjacent ion channels may serve to propagate an action potential along the length of the neuron. Further, the activation of an ion channel in an individual neuron may induce the activation of ion channels in neighboring neurons that, bundled together, form nerve tissue. The activation of a single ion channel in a single neuron, however, may not be sufficient to induce the cascading activation of neighboring ion channels necessary to permit the propagation of an action potential. Thus, the more ion channels in a locality that may be recruited by an initial potential difference, caused through natural means such as the action of nerve endings or through artificial means, such as the application of electric fields, the more likely the propagation of an action potential may be. The process of artificially inducing the propagation of action potentials along the length of a nerve may be referred to as stimulation, or up modulation.

Neurons may also be prevented from functioning naturally through constant or substantially constant application of a voltage potential difference. After activation, each ion channel experiences a refractory period, during which it "resets" the sodium and potassium concentrations across the plasma membrane back to an initial state. Resetting the sodium and potassium concentrations causes the membrane threshold potential to return to an initial state. Until the ion channel restores an appropriate concentration of sodium and potassium across the plasma membrane, the membrane threshold potential will remain elevated, thus requiring a higher voltage potential to cause activation of the ion channel. If the membrane threshold potential is maintained at a high enough level, action potentials propagated by neighboring ion channels may not create a large enough voltage potential difference to surpass the membrane threshold potential and activate the ion channel. Thus, by maintaining a sufficient voltage potential difference in the vicinity of a particular ion channel, that ion channel may serve to block further signal transmission. The membrane threshold potential may also be raised without eliciting an initial activation of the ion channel. If an ion channel (or a plurality of ion channels) are subjected to an elevated voltage potential difference that is not high enough to surpass the membrane threshold potential, it may serve to raise the membrane threshold potential over time, thus having a similar effect to an ion channel that has not been permitted to properly restore ion concentrations. Thus, an on channel may be recruited as a block without actually causing an initial action potential to propagate. This method may be valuable, for example, in pain management, where the propagation of pain signals is undesired. As described above with respect to stimulation, the larger the number of ion channels in a locality that may be recruited to serve as blocks, the more likely the chance that an action potential propagating along the length of the nerve will be blocked by the recruited ion channels, rather than traveling through neighboring, unblocked channels.

The number of ion channels recruited by a voltage potential difference may be increased in at least two ways. First, more ion channels may be recruited by utilizing a larger voltage potential difference in a local area. Second, more ion channels may be recruited by expanding the area affected by the voltage potential difference.

Returning to FIG. 6a, it can be seen that, due to the electric field lines 220 running in a direction substantially parallel to the longitudinal direction of the nerve 210, a large portion of nerve 210 may encounter the field. Thus, more ion channels from the neurons that make up nerve 210 may be recruited without using a larger voltage potential difference. In this way, modulation of nerve 210 may be achieved with a lower current and less power usage. FIG. 6b illustrates an embodiment wherein electrodes 158a and 158 are still spaced apart from one another in a longitudinal direction of at least a portion of nerve 210. A significant portion of nerve 210 remains inside of the electric field. FIG. 6c illustrates a situation wherein electrodes 158a and 158b are spaced apart from one another in a transverse direction of nerve 210. In this illustration, it can be seen that a significantly smaller portion of nerve 210 will be affected by electric field lines 220.

Figure 7:
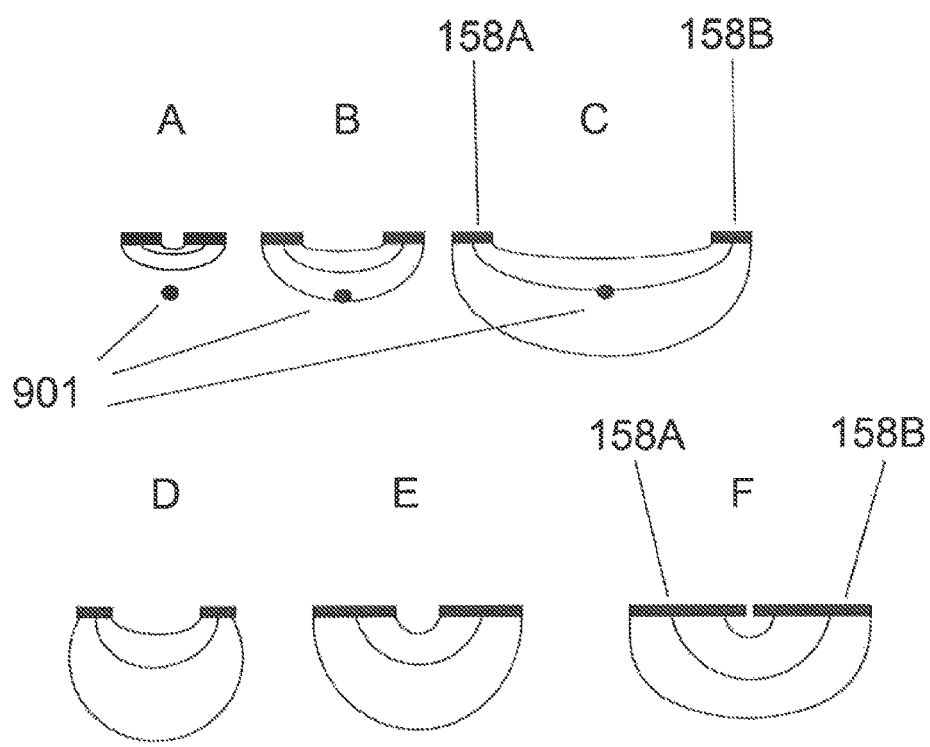
FIG. 7 illustrates effects of electrode configuration on the shape of a generated electric field.

FIG. 7 illustrates potential effects of electrode configuration on the shape of a generated electric field. The top row of electrode configurations, e.g., A, B, and C, illustrates the effects on the electric field shape when a distance between electrodes of a constant size is adjusted. The bottom row of electrode configurations, e.g., D, E, and F illustrates the effects on the electric field shape when the size of electrodes of constant distance is adjusted.

In embodiments consistent with the present disclosure, modulation electrodes 158a, 158b may be arranged on the surface of a muscle or other tissue, in order to modulate a nerve embedded within the muscle or other tissue. Thus, tissue may be interposed between modulation electrodes 158a. 158b and a nerve to be modulated. Modulation electrodes 158a, 158b may be spaced away from a nerve to be modulated. The structure and configuration of modulation electrodes 158a, 158b may play an important role in determining whether modulation of a nerve, which is spaced a certain distance away from the electrodes, may be achieved.

Electrode configurations A, B, and C show that when modulation electrodes 158a, 158b of a constant size are moved further apart, the depth of the electric field facilitated by the electrodes increases. The strength of the electric field for a given configuration may vary significantly depending on a location within the field. If a constant level of current is passed between modulation electrodes 158a and 158b, however, the larger field area of configuration C may exhibit a lower overall current density than the smaller field area of configuration A. A lower current density, in turn, implies a lower voltage potential difference between two points spaced equidistant from each other in the field facilitated by configuration C relative to that of the field facilitated by configuration A. Thus, while moving modulation electrodes 158a and 158b farther from each other increases the depth of the field, it also decreases the strength of the field. In order to modulate a nerve spaced away from modulation electrodes 158a, 158b, a distance between the electrodes may be selected in order to facilitate an electric field of strength sufficient to surpass a membrane threshold potential of the nerve (and thereby modulate it) at the depth of the nerve. If modulation electrodes 158a, 158b are too close together, the electric field may not extend deep enough into the tissue in order to modulate a nerve located therein. If modulation electrodes 158a, 158b are too far apart, the electric field may be too weak to modulate the nerve at the appropriate depth.

Appropriate distances between modulation electrodes 158a, 158b, may depend on an implant location and a nerve to be stimulated. For example, modulation point 901 is located at the same depth equidistant from the centers of modulation electrodes 158a, 158b in each of configurations A, B, and C, The figures illustrate that, in this example, configuration B is most likely to achieve the highest possible current density, and therefore voltage potential, at modulation point 901. The field of configuration A may not extend deeply enough, and the field of configuration C may be too weak at that depth.

In some embodiments, modulation electrodes 158a, 158b may be spaced apart by about a distance of about 0.2 mm to 25 mm. In additional embodiments, modulation electrodes 158a, 158b may be spaced apart by a distance of about 1 mm to 10 mm, or between 4 mm and 7 mm. In other embodiments modulation electrodes 158a, 158b may be spaced apart by between approximately 6 mm and 7 mm.

Electrode configurations D, E, and F show that when modulation electrodes 158a, 158b of a constant distance are changed in size, the shape of the electric field facilitated by the electrodes changes. If a constant level of current is passed between when modulation electrodes 158a and 158b, the smaller electrodes of configuration D may facilitate a deeper field than that of configurations E and F, although the effect is less significant relative to changes in distance between the electrodes. As noted above, the facilitated electric fields are not of uniform strength throughout, and thus the voltage potential at seemingly similar locations within each of the electric fields of configurations D, E, and, F may vary considerably. Appropriate sizes of modulation electrodes 158a, 158b, may therefore depend on an implant location and a nerve to be stimulated.

In some embodiments, modulation electrodes 158a, 158b may have a surface area between approximately 0.01 mm$^2$ and 80 mm$^2$. In additional embodiments, modulation electrodes 158a, 158b may have a surface area between approximately 0.1 mm$^2$ and 4 mm$^2$. In other embodiments modulation electrodes 158a, 158b may have a surface area of between approximately 0.25 mm$^2$ and 0.35 mm$^2$.

In some embodiments, modulation electrodes 158a, 158b may be arranged such that the electrodes are exposed on a single side of carrier 161. In such an embodiment, an electric field is generated only on the side of carrier 161 with exposed electrodes. Such a configuration may serve to reduce the amount of energy required to achieve neural modulation, because the entire electric field is generated on the same side of the carrier as the nerve, and little or no current is wasted traveling through tissue away from the nerve to be modulated. Such a configuration may also serve to make the modulation more selective. That is, by generating an electric field on the side of the carrier where there is a nerve to be modulated, nerves located in other areas of tissue (e.g., on the other side of the carrier from the nerve to be modulated), may avoid being accidentally modulated.

As discussed above, the utilization of electric fields having electrical field lines extending in a direction substantially parallel to the longitudinal direction of a nerve to be modulated may serve to lower the power requirements of modulation. This reduction in power requirements may permit the modulation of a nerve using less than 1.6 mA of current, less than 1.4 mA of current, less than 1.2 mA of current, less than 1 mA of current, less than 0.8 mA of current, less than 0.6 mA of current, less than 0.4 mA of current, and even less than 0.2 mA of current passed between modulation electrodes 158a, 158b.

Reducing the current flow required may have additional effects on the configuration of implant unit 110 and external unit 120. For example, the reduced current requirement may enable implant unit 110 to modulate a nerve without a requirement for a power storage unit, such as a battery or capacitor, to be implanted in conjunction with implant unit 110. For example, implant unit 110 may be capable of modulating a nerve using only the energy received via secondary antenna 152, Implant unit 110 may be configured to serve as a pass through that directs substantially all received energy to modulation electrodes 158a and 158b for nerve modulation. Substantially all received energy may refer to that portion of energy that is not dissipated or otherwise lost to the internal components of implant unit 110. Finally, the reduction in required current may also serve to reduce the amount of energy required by external unit 120. External unit 120 may be configured to operate successfully for an entire treatment session lasting from one to ten hours by utilizing a battery having a capacity of less than 240 mAh, less than 120 mAh, and even less than 60 mAh.

As discussed above, utilization of parallel fields may enable implant unit 110 to modulate nerves in a non-contacting fashion, Contactless neuromodulation may increase the efficacy of an implanted implant unit 110 over time compared to modulation techniques requiring contact with a nerve or muscle to be modulated. Over time, implantable devices may migrate within the body. Thus, an implantable device requiring nerve contact to initiate neural modulation may lose efficacy as the device moves within the body and loses contact with the nerve to be modulated. In contrast, implant unit 110, utilizing contactless modulation, may still effectively modulate a nerve even if it moves toward, away, or to another location relative to an initial implant location. Additionally, tissue growth and/or fibrosis may develop around an implantable device. This growth may serve to lessen or even eliminate the contact between a device designed for contact modulation and a nerve to be modulated. In contrast, implant unit 110, utilizing contactless modulation, may continue to effectively modulate a nerve if additional tissue forms between it and a nerve to be modulated.

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. For example, components including diodes may be included in implant unit 110 or in external unit 120 to limit power transferred from the external unit 120 to the implant unit 110. In some embodiments, diode 156 may function to limit the power level received by the patient. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110. Because external unit 120 may be manually placed on the body, the relative location and distance between primary antenna 150 and secondary antenna 152 may vary from usage to usage. It may thus provide a benefit for processor 144 to determine a degree of coupling and determine an efficiency of energy transfer in order to transmit an appropriate amount of power to modulate a nerve to the appropriate degree.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular vein (i.e., in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal (i.e., a down modulation) at the electrodes, thereby inhibiting a signal to raise blood pressure carried from the renal nerves to the kidneys.

A modulation control signal may be pre-programmed, Such a pre-programmed modulation control signal may result from instructions provided to external unit 120. Such instructions may be provided, for example, by a subject's physician, and may be based on various factors, such as measured blood pressure. Such instructions may be updated daily, weekly, monthly, or at any other interval that is appropriate.

In other embodiments, the modulation control signal may be dynamically determined based on concurrent blood pressure data received by the external unit 120. Such data may be collected by a sensor associated with implant unit 110 or by a sensor unassociated with implant unit 110. Such data may be transmitted to external unit 120 via a radiofrequency antenna, using means described herein.

Modulation control signals may include stimulation and inhibition control signals, and sub-modulation control signals may include sub-stimulation and sub-inhibition control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.02 and 2 seconds. In some embodiments, there may be no separation between pulses. For example, in a pulse train of 200 millisecond pulses, each separated by 0.1 seconds from the next, a new pulse will occur every 0.3 seconds. A pulse train of this embodiment may be utilized, for example, to provide ongoing inhibition or stimulation during a treatment session. In the context of hypertension, a treatment session may be a period of time during which a subject uses an external unit 120 to apply a modulation control signal. Such a treatment session may last anywhere from a few hours to a few days, or may even be continuous for longer periods of time. In the context of other conditions to which neural modulators of the present disclosure are applied, a treatment session may be of varying length according to the duration of the treated condition.

The configuration of a pulse train, as described herein, may be altered for the purpose of stimulation (e.g., in the case of the glossopharyngeal nerve, as described above) or inhibition (e.g., in the case of a renal nerve). Pulse trains utilized for stimulation and for inhibition may require varying parameters. For example, pulse trains utilized for inhibition may require longer pulses and sub-pulses, so as to prevent a nerve cell from recovering its action potential. Pulse trains utilized for inhibition may require lower amplitude signals, as it is only necessary to create a blockage, rather than to cause signal propagation.

In some embodiments, a modulation control signal, rather than include a pulse train of discrete pulses, may include a consistent alternating current signal. Such an alternating current signal may prove sufficient to inhibit the propagation of nerve signals.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be used as a basis for alerting the subject if the external unit becomes dislodged or moves in any other manner (e.g., vibration, etc.), altering the coaxial, lateral, or angular offset between primary antenna 150 and secondary antenna 152. As a result of such movement, the degree of coupling between primary antenna 150 and secondary antenna 152 may change, and the voltage level or current level of the primary coupled signal component on primary antenna 150 may also change. Additionally, processor 144 may be configured to recall a baseline coupling level from a previous treatment session. A recalled baseline coupling level may be used to more accurately determine an amount of energy required for head pain treatment in a current session, as explained further below.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

In some embodiments, processor 144 may employ an iterative process in order to select modulation control signal parameters that result in a desired response level. A subject's blood pressure may be monitored, for example, by means of an external blood pressure monitor. Processor 144 may then begin nerve modulation, either stimulation or inhibition depending on an implant location, at an initial level. As the subject, or a physician, monitors the subject's blood pressure, the level of modulation control that is applied by processor 144 via implant unit 110 may be increased until a desired level of response is achieved. In some embodiments, this process may occur over several hours or several days, with the subject measuring their blood pressure every few hours and indicating the current blood pressure level to processor 144. Processor 144 may be configured to recall the parameters of the modulation control signal required by the patient to provide a sufficient therapy level. When processor 144 is configured to recall a baseline coupling level and a therapy sufficient modulation control signal, it may use this information, when activated in a subsequent session, to select an initial modulation control signal.

In one mode of operation, processor 144 may be configured to sweep over a range of parameter values until nerve modulation is achieved. For example, when a patient has indicated to processor 144 that nerve inhibition is necessary, processor 144 may select a modulation control signal providing an initial amount of nerve inhibition. The amplitude and/or pulse duration (or other parameters) associated with the signal applied to primary antenna 150 may be iteratively increased by predetermined amounts and at a predetermined rate until the subject or subject's physician indicates that a therapeutic amount of nerve inhibition has occurred.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of power from the external unit to the implant unit based on the determined degree of coupling.

In some embodiments, implant unit 110 may include a processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to and external unit. Power for the processor unit may be supplied by an onboard power source or received from a physically disconnected power source via transmissions from an external unit.

In other embodiments, implant unit 110 may be self-sufficient, including its own power source and a processor configured to operate the implant unit 110 with no external interaction. For example, with a suitable power source, the processor of implant unit 110 could be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

In some embodiments, the at least one processor may be associated with the housing of external unit 120 and may be configured to communicate with a circuit implanted in the subject. The at least one processor may also be configured to receive a physiological signal from the subject via the implanted circuit. In response to the received physiological signal, the at least one processor may send a control signal, such as a closed loop control signal, to the implanted circuit. In some embodiments, the control signal may be predetermined to activate neuromuscular tissue within the body. Activating neuromuscular tissue may include, for example, causing initiating or blocking a nerve action potential.

The physiological signal received from the implant unit may include any signal or signal component indicative of at least one physiological characteristic associated with the subject. In some embodiments, for example, the physiological characteristic may indicate blood pressure and/or a change in blood pressure. The physiological signal may include any form of signal suitable for conveying information associated with at least some aspect of the subject. In some embodiments, the physiological signal may include an electromagnetic signal (e.g., microwave, infrared, radiofrequency (RF), etc.) having any desired waveform (e.g., sinusoidal, square wave, triangle wave, etc.). In some embodiments, the physiological signal may include any suitable amplitude or duration for transferring information about the subject.

In some embodiments, the physiological signal may include a primary coupled signal component on primary antenna 150. This primary coupled signal component may be induced on primary antenna 150 through coupling between primary antenna 150 of external unit 120 and secondary antenna 152 on implant unit 110.

In some embodiments, the physiological signal may include at least one aspect indicative of a subject's blood pressure. For example, blood pressure may be detected directly, through a pressure sensor included in implant unit 110 or implanted elsewhere in the body. A signal indicative of blood pressure may also be detected indirectly, for example via sensors measuring neural activity in the glossopharyngeal or renal nerves. Blood pressure may also be detected by an external source, for example via a blood pressure cuff or other external measurement device. As noted, in response to a received physiological signal, the at least one processor may cause a response based on the physiological signal. For example, in some embodiments, the at least one processor may be configured to cause the generation of a control signal (e.g., a closed loop control signal) intended to control at least one aspect of implant unit 110. The control signal may include a modulation control signal applied to primary antenna 150 such that a resulting secondary signal on secondary antenna 152 will provide a modulation signal at implant electrodes 158a and 158b.

In some embodiments, the processor may be configured to detect blood pressure or a change in blood pressure based on the physiological signal and send the closed loop control signal in response to the detected blood pressure or change in blood pressure. The at least one processor may be further configured to determine a severity of the blood pressure or change in blood pressure event based on the physiological signal and vary a power level or duration of the control signal based on the determined severity of the blood pressure or change in blood pressure. The severity of the blood pressure or change in blood pressure may be determined, for example, based on measurements as discussed above. In some embodiments, a control signal may be sent if the blood pressure or change in blood pressure exceeds a certain threshold.

A control signal may include any signal having suitable characteristics for causing a desired response in implant unit 110. For example, a control signal may have any suitable amplitude, duration, pulse width, duty cycle, or waveform (e.g., a sinusoidal signal, square wave, triangle wave, etc.) for causing a desired effect on implant unit 110 (e.g., modulation of nerve tissue in the vicinity of implant unit 110, etc.). A control signal may be generated and sent (e.g., to implant unit 110) within any desired response time relative to receipt of a physiological signal. In some embodiments, the response time may be set at 1 second, 500 milliseconds, 200 milliseconds, 100 milliseconds, 50 milliseconds, 20 milliseconds, 5 milliseconds, 1 millisecond, or any other time greater than 0 seconds and less than about 2 seconds. The control signal may be closed loop. As used herein, the term closed loop control signal may refer to any signal at least partially responsive to another signal, such as a control signal sent in response to a physiological signal. Or it may include any feedback response.

Based on the physiological signal, the processor may determine a quantity of energy to be sent via the closed loop control signal to implant unit 110. The amount of energy to be sent may be determined and/or varied based on any relevant factor including, for example, the time of day, a relevant biological factor of the subject (blood pressure, pulse, level of brain activity, etc.), the severity of the detected event, other characteristics associated with the detected event, or on any combination of factors. As noted, in embodiments where the physiological signal indicates blood pressure or change in blood pressure, the processor may be configured to determine a severity of the blood pressure or change in blood pressure based on the physiological signal. In such embodiments, the processor may also determine an amount of energy to be provided to implant unit 110 as a response to the detected blood pressure or change in blood pressure and in view of the determined severity of the event. The determined amount of energy may be transferred to implant unit 110 over any suitable time duration and at any suitable power level. In some embodiments, the power level and/or the duration of the control signal may be varied, and such variation may be dependent on the determined severity of the blood pressure or change in blood pressure.

The power level and/or duration of the control signal may also be determined based on other factors. For example, the processor may vary a power level or duration associated with the control signal based on the efficiency of energy transfer between external unit 120 and implant unit 110. The processor may have access to such information through pre-programming, lookup tables, information stored in memory, etc. Additionally or alternatively, the processor may be configured to determine the efficiency of energy transfer, e.g., by monitoring the primary coupled signal component present on primary antenna 150, or by any other suitable method.

The processor may also vary the power level or duration of the control signal based on the efficacy of implant unit 110 (e.g., the implant unit's ability to produce a desired effect in response to the control signal). For example, the processor may determine that a certain implant unit 110 requires a certain amount of energy, a control signal of at least a certain power level and/or signal duration, etc., in order to produce a desired response (e.g., a modulation signal having an amplitude/magnitude of at least a desired level, etc.). Such a determination can be based on feedback received from implant unit 110 or may be determined based on lookup tables, information stored in memory, etc. In some embodiments, the power level or duration of the control signal may be determined based on a known or feedback-determined efficacy threshold (e.g., an upper threshold at or above which a desired response may be achieved) associated with implant unit 110.

Figure 8:
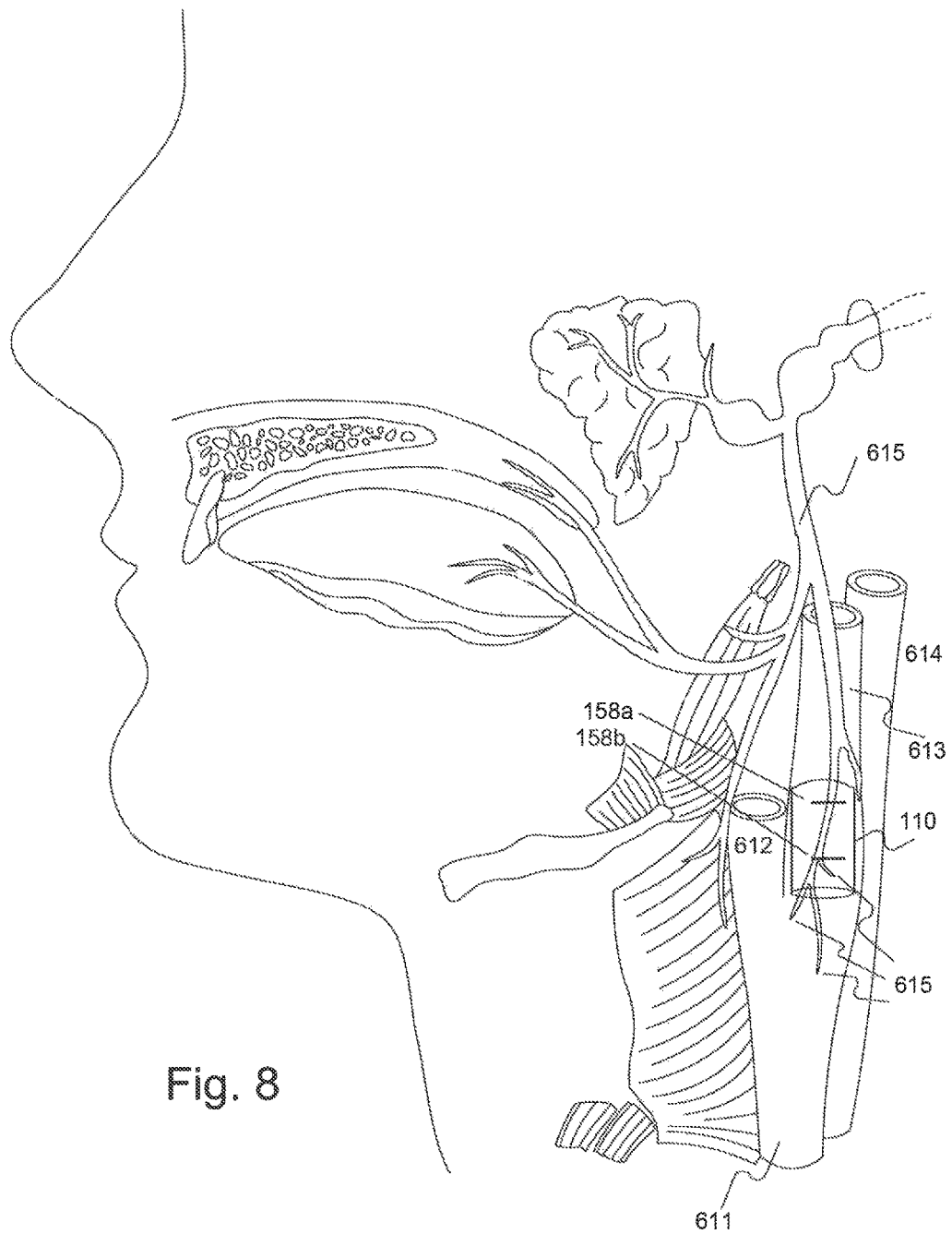
FIG. 8 depicts an exemplary implant location for the t ea ent of hypertension.

In some embodiments, implant unit 110 may be structurally configured to facilitate implantation in a location so as to increase the efficacy of modulation provided. For example, FIGS. 8 and 9 illustrate exemplary implant units 110 structurally configured for the treatment of hypertension.

Electrodes 158a, 158b, of implant unit 110 may be configured to generate a parallel electric field 1090, sufficient to cause modulation of afferent neurons carrying blood pressure signals even when electrodes 158a, 158b are not in contact with the fibers of the nerve. That is, the anodes and the cathodes of the implant may be configured such that, when energized via a circuit associated with the implant 110 and electrodes 158a, 158b, the electric field 1090 extending between electrodes 158a, 158b may be in the form of a series of substantially parallel arcs extending through and into the muscle tissue on which the implant is located. A pair of parallel line electrodes or two series of circular electrodes may be suitable configurations for producing the appropriate parallel electric field lines. Thus, when suitably implanted, the electrodes of implant unit 110 may modulate a nerve in a contactless fashion, through the generation of parallel electric field lines.

Furthermore, the efficacy of modulation may be increased by an electrode configuration suitable for generating parallel electric field lines that run partially or substantially parallel to nerve fibers to be modulated. In some embodiments, the current induced by parallel electric field lines may have a greater modulation effect on a nerve fiber if the electric field lines 220 and the nerve fibers to be modulated are partially or substantially parallel.

In order to facilitate the modulation of afferent nerve fibers transmitting blood pressure signals, implant unit 110 may be designed or configured to ensure the appropriate location of electrodes when implanted. An exemplary implantation is depicted in FIGS. 8 and 9.

For example, a flexible carrier 161 of the implant may be configured for location in the interior of a blood vessel, such that electrodes 158a and 158b may be in a position to modulate a nerve located outside of the interior of the blood vessel. In some embodiments, a nerve located outside of the interior of the blood vessel may be located in tissue in the wall of the blood vessel. FIG. 8 depicts an exemplary implant location for the treatment of hypertension. As illustrated in FIG. 8, implant unit 110110 may be configured for location or implantation inside a blood vessel. Such a configuration may include, for example, a flexible tubular carrier. A flexible tubular carrier, may include, for example, a stent, or an expandable stent. Various aspects of implant unit 110 are illustrated in FIGS. 4a and 4b, which show an exemplary embodiment of implant unit 110 from two different views. 110152 Implant unit 110 may include modulation electrodes 158a, 158b configured to facilitate an electric field including field lines extending in the longitudinal direction of the blood vessel. For example, as illustrated in FIG. 8, implant unit 110 may be implanted in a carotid artery 611. Implant unit 110 may be located within carotid artery 611 in a location in the vicinity of carotid baroreceptors 615, at a location near the branching of the internal carotid artery 613 and the external carotid artery 612. As described previously, carotid baroreceptors 615 aid in the regulation of the blood pressure of a subject. Thus, implant unit 110, located within carotid artery 611 in the vicinity of carotid baroreceptors 615 may facilitate an electric field configured to modulate carotid baroreceptors 615 and or the glossopharyngeal nerve, to which the carotid baroreceptors 615 deliver a blood pressure signal, and, thus, affect the blood pressure of a subject.

Affecting the blood pressure of a subject may include reducing, increasing, controlling, regulating, and influencing the blood pressure of a subject. The illustrated location is exemplary only, and implant unit 110 may be configured in alternate ways. For example, implant unit 110 may be configured for implantation in jugular vein 614 of the subject, in a location from which modulation of carotid baroreceptors 615 may be accomplished. Furthermore, implant unit 110 may be configured for implantation in a blood vessel, such as carotid artery 611 or jugular vein 614, in a location suitable for modulation of glossopharyngeal nerve 615 in an area located away from the carotid baroreceptors. As described above, glossopharyngeal nerve 615 innervates carotid baroreceptors 615. Thus, glossopharyngeal nerve 615 may be directly modulated to affect blood pressure of a subject. Glossopharyngeal nerve 615 may also be modulated by an implant unit 110 located sub-cutaneously, in a non-intravascular location.

FIG. 9 depicts another exemplary implant location for the treatment of hypertension. As illustrated in FIG. 9, implant unit 110 may be configured for location or implantation inside a blood vessel. Such a configuration may include, for example, a flexible tubular carrier. 110 Implant unit 110 may include modulation electrodes 158a, 158b configured to facilitate an electric field including field lines extending in the longitudinal direction of the blood vessel. For example, as illustrated in FIG. 9, implant unit 110 may be implanted in a renal artery 711. Implant unit 110 may be located within renal artery 711 in a location in the vicinity of renal nerves 715 surrounding renal artery 711 prior to its entry into kidney 712. As described previously, renal nerves 715 aids in the regulation of the blood pressure in humans. Thus, implant unit 110, located within renal artery 711 in the vicinity of renal nerves 715 may facilitate an electric field configured to modulate renal nerves 715, and, thus, affect the blood pressure of a subject. The illustrated location is exemplary only, and implant unit 110 may be configured in alternate ways suitable for the modulation of renal nerves 715. Modulation of the renal nerves 715 by an implant unit 110 may take the form of continuous or as-needed nerve blocking, as described above. This modulation may be adjusted, on a continuous or periodic basis, by an external device, for example, to increase or decrease the level of treatment in response to the patient's blood pressure changes. This may be done in nearly real-time, by constantly measuring blood pressure, or may be accomplished more periodically, by measuring blood pressure at regular intervals, such as daily, weekly, monthly, and yearly.

Implant unit 1110 may be delivered, via catheter, to a location inside the carotid artery or the jugular vein of a subject. Access to the carotid artery may be gained via the axillary artery with no requirement for the catheter to traverse the heart.

In some embodiments, implant unit 110 may include means for orientation after catheter based delivery to an intravascular implantation location. Such means may include, for example, a radiopaque marker deployed with the carrier, and arranged in a fixed position with respect to the secondary antenna of implant unit 110. Thus, using imaging techniques for viewing the radiopaque marker during implantation, the positioning of the antenna could be optimized. Alternatively, an implant unit 110 containing no radiopaque marker may be deployed to an intravascular location, and measurements of coupling, as described above, may be made to determine an optimized implantation location and orientation.

In an additional embodiment, an implant unit may be simplified to eliminate some elements of the circuitry contained therein. A frequency modulation method using a radiofrequency signal at a relatively high frequency as a carrier wave may be used to transmit a lower frequency signal to an implanted device in order to cause neural stimulation with the lower frequency signal. Transmitting a frequency modulated signal in this fashion may involve use of a filter on the receiving end to filter out the high frequency signal in order to convey the low frequency signal to the electrodes for stimulation. Filters of this type typically may include a capacitive element. In order to create a more efficient device, the capacitive elements on the circuit may be eliminated and the circuit may be configured to employ the surrounding tissue as the required filter element. One method of generating the transmitted signal may include transmitting the radiofrequency signal in pulses less than about 300 microseconds. When received by the implant, the modulated signal may be passed directly to the tissue to be stimulated, which may act as a filter to remove the high frequency components of the signal, thereby allowing the lower frequency components to cause stimulation. In such an embodiment, implant unit 110 may include only a single electrode 158*a*, configured to function as either a cathode or anode, while tissue of the patient serves as the other of the cathode and anode.

Modulation of the renal nerves 715 may also take the form of induced temporary nerve paralysis. If implant unit 110 delivers a sufficiently large modulation signal to renal nerves 715, renal nerves 715 may cease to propagate signals for a period of several hours to several days. Such a modulation signal may be delivered as an alternating current energy signal Thus, a method of treating hypertension, or any other condition affected by a nerve, may include orienting a power source external to a body and adjacent to a location within the body where an implant unit 110 is located to a position from which implant unit 110 may receive transmitted power, and, no more than three times a day, wirelessly transmitting an alternating current signal to implant unit 110 to cause temporary nerve paralysis. Such a signal may be shorter than 10 seconds, and may deliver at least two watts of energy.

In alternative embodiments, implant unit 110, configured for vasculature implantation, may also be delivered to the cerebral vasculature to stimulate regions of the brain and/or to receive feedback from the brain in a minimally invasive manner. The device could be delivered temporarily or permanently.

FIG. 10 illustrates an apparatus for catheter delivery of an ablation apparatus. FIG. 10 depicts a carrier having a plurality of electrode contacts 1701 arranged circumferentially about it. In the exemplary embodiment of FIG. 10, the carrier 1702, configured for intravascular deployment, includes an expandable balloon-like device. In alternative embodiments the carrier 1702 may be an expandable mesh. The carrier 1702 may include as many as 10, 20, 30, 40, or more electrode contacts 1701, arranged both circumferentially and axially. When the carrier is expanded, the plurality of electrode contacts 1701 are pressed against the wall of the vascular structure in which the carrier 1702 is located. This expansion serves to create a predictable pattern of electrode contact with the vessel wall. At the same time, a return electrode is placed on the skin of the patient to complete an electrical circuit. When the electrodes 1701 are subsequently energized, electricity is conducted from the plurality of electrodes 1701 through the surrounding tissue to the return electrode placed on the skin of the patient. The conducted electricity serves to cause thermal damage (e.g., ablation) to the tissue immediately surrounding the electrodes. As described above, the renal nerves 715 may surround renal artery 711. The uniform electrode pattern may facilitate a uniform ablation of the renal nerves 715. In this fashion, the operator of the device may be assured that most or all of renal nerves 715 are sufficiently ablated to prevent the conduction of any further blood pressure control signals. As blood pressure control signals from the renal nerves 715 serve to raise blood pressure, renal nerve ablation may contribute to a reduction in blood pressure.

Other embodiments of the present disclosure will be apparent to those skilled in the art from consideration of the specification and practice of the present disclosure.

While this disclosure provides examples of neuromodulation devices employed for the treatment of certain conditions, usage of the disclosed neuromodulation devices is not limited to the disclosed examples. The disclosure of uses of embodiments of the invention for energy delivery to nerves are to be considered exemplary only. In its broadest sense, the invention may be used in connection with the treatment of any physiological condition through the delivery of energy to nerves. Alternative embodiments will become apparent to those skilled in the art to which the present invention pertains without departing from its spirit and scope. Accordingly, the scope of the present invention is defined by the appended claims rather than the foregoing description.

What is claimed is:
1. A hypertension therapy device, comprising:
   a carrier configured for deployment in vasculature of a subject;
   an antenna located on the carrier;
   at least one electrode arranged for deployment with the carrier, the at least one electrode being arranged so as to create an electric field when the electrode is energized;
   at least a portion of a circuit arranged for intravascular deployment with the carrier within a blood vessel, the circuit portion being electrically connected to the at least one electrode, the circuit portion further being configured to:
   generate a physiological signal indicating a change in a subject's blood pressure; and
   receive a control signal configured to, when the change in the subject's blood pressure exceeds a predetermined threshold, cause an electrical signal providing an initial amount of nerve inhibition to be delivered to the at least one electrode and cause an amplitude and a pulse duration of the electrical signal to be iteratively increased by a predetermined amount at a predetermined rate until a desired amount of nerve inhibition occurs; and
   wherein the at least one electrode is configured to emit from within an interior of the blood vessel an electrical field sufficient to modulate signals of at least one nerve located outside of the interior of the blood vessel the vasculature, and wherein the at least one electrode includes a plurality of electrode contacts arranged in subsets, the electrode contacts within each subset being electrically connected to each other.

2. The device of claim 1, wherein the at least one electrode serves as one of a cathode or an anode, and wherein tissue of a patient serves as another of the anode and the cathode.

3. The device of claim 1, wherein the at least one electrode includes a conductive loop.

4. The device of claim 1, wherein the carrier includes a stent and the at least one pair of electrodes and the circuit portion are deployed on the stent.

5. The device of claim 1, wherein the at least one electrode is configured to emit a unidirectional electrical field.

6. The device of claim 1, wherein the field sufficient to modulate is a field configured to block nerve transmission.

7. The device of claim 1, wherein the field sufficient to modulate is a field configured to augment a nerve transmission.

8. The device of claim 1, wherein the at least one electrode and the circuit portion are configured so that when the carrier is implanted in a carotid artery adjacent a baroreceptor the unidirectional electrical field is shaped to modulate the subject's baroreflex via augmenting a nerve transmission.

9. The device of claim 1, wherein the carrier is configured for substantially permanent implantation in the vasculature.

10. The device of claim 1, wherein the carrier is configured for temporary location in the vasculature and for removal following a period of modulation.

11. The device of claim 1, wherein the at least one electrode and the circuit portion are configured so that when the carrier is implanted in a carotid artery adjacent a glossopharyngeal nerve, the electrical field is shaped to modulate the glossopharyngeal nerve.

12. The device of claim 1, wherein the at least one electrode and the circuit portion are configured so that when the carrier is implanted in a jugular vein in a vicinity of a glossopharyngeal nerve, the electrical field is shaped to modulate the glossopharyngeal nerve.

13. The device of claim 1, wherein the at least one electrode and the circuit portion are configured so that when the carrier is implanted in a renal artery in a vicinity of a renal nerve, the electrical field is shaped to modulate the renal nerve.

14. The device of claim 1, wherein the at least one electrodes and the circuit portion are configured so that when the carrier is implanted in a renal artery in a vicinity of a sympathetic renal nerve, the electrical field is shaped to modulate the sympathetic renal nerve.

15. The device of claim 1, wherein the circuit portion is configured to receive power wirelessly from a source external to the subject.

16. An intravascular device for hypertension therapy, comprising:

a carrier configured for deployment in a blood vessel via an intravascular deployment mechanism; and a plurality of electrode contacts arranged circumferentially about the carrier;

wherein the electrode contacts are configured to receive energy from a source and to radiate energy via the plurality of electrical contacts to a plurality of locations on a wall of the blood vessel, wherein the electrode contacts are arranged in subsets, the electrode contacts within each subset being electrically connected to each other, and a circuit electrically connected to the electrode contacts and configured to:

generate a physiological signal indicating a change in a subject's blood pressure; and receive a control signal configured to, when the change in the subject's blood pressure exceeds a predetermined threshold, cause an electrical signal providing an initial amount of nerve inhibition to be delivered to the electrode contacts and cause an amplitude and a pulse duration of the electrical signal to be iteratively increased by a predetermined amount at a predetermined rate until a desired amount of nerve inhibition occurs.

17. The device of claim 16, wherein at least a portion of the electrode contacts are configured to radiate energy substantially simultaneously to a plurality of locations on a wall of the blood vessel.

18. The device of claim 16, wherein at least a portion of the electrode contacts are configured to radiate energy to at least one nerve outside the interior of the blood vessel via the blood vessel wall.

19. The device of claim 16, wherein the carrier is expandable to a position that enables the plurality of electrode contacts to make contact with the vessel wall.

20. The device of claim 16, wherein the carrier is a balloon.

21. The device of claim 16, wherein the electrode contacts are arranged on the balloon.

22. The device of claim 16, wherein the carrier is an expandable mesh.

23. The device of claim 16, wherein the electrode contacts are configured to radiate ablative energy.

24. The device of claim 16, wherein the carrier includes an insulator and the contacts protrude through openings in the insulator.

25. The device of claim 16, wherein each subset of electrode contacts is part of a single elongated electrode and wherein a plurality of first portions of the single electrode are insulated to prevent the plurality of first portions from contacting the vessel wall, and wherein a plurality of second portions of the electrode are exposed to permit the plurality of second portions to contact the vessel wall.

26. The device of claim 16, further comprising a balloon, and wherein the carrier is flexible and designed to expand in response to inflation of the balloon.

27. The device of claim 16, further comprising a mesh of flexible electrodes.

* * * * *

UNITED STATES PATENT AND TRADEMARK OFFICE
CERTIFICATE OF CORRECTION

PATENT NO. : 10,238,875 B2  
APPLICATION NO. : 14/653891  
DATED : March 26, 2019  
INVENTOR(S) : Adi Mashiach Page 1 of 1

It is certified that error appears in the above-identified patent and that said Letters Patent is hereby corrected as shown below:

In the Claims

Claim 1, Column 29, Lines 2-3, delete "the vasculature".

Claim 8, Column 29, Line 25, "baroreceptor the" should read -- baroreceptor, the --.

Signed and Sealed this  
Fourth Day of June, 2019

Andrei Iancu  
*Director of the United States Patent and Trademark Office*